(12) United States Patent
Meier et al.

(10) Patent No.: US 8,350,022 B2
(45) Date of Patent: Jan. 8, 2013

(54) METHOD FOR THE STEREOSELECTIVE SYNTHESIS OF PHOSPHORUS COMPOUNDS

(75) Inventors: Chris Meier, Jork (DE); Jens O. Thomann, Cappeln (DE)

(73) Assignee: Universitaet Hamburg, Hamburg (DE)

( * ) Notice: Subject to any disclaimer, the term of this patent is extended or adjusted under 35 U.S.C. 154(b) by 291 days.

(21) Appl. No.: 12/935,073

(22) PCT Filed: Apr. 3, 2009

(86) PCT No.: PCT/DE2009/000437
§ 371 (c)(1),
(2), (4) Date: Sep. 28, 2010

(87) PCT Pub. No.: WO2009/121347
PCT Pub. Date: Oct. 8, 2009

(65) Prior Publication Data
US 2011/0028705 A1    Feb. 3, 2011

(30) Foreign Application Priority Data

Apr. 4, 2008    (DE) .......................... 10 2008 017 500

(51) Int. Cl.
*C07H 21/00* (2006.01)
(52) U.S. Cl. .................................... 536/25.33; 536/25.3
(58) Field of Classification Search .................. None
See application file for complete search history.

(56) References Cited

U.S. PATENT DOCUMENTS

2010/0174079 A1    7/2010    Han et al.

FOREIGN PATENT DOCUMENTS

| JP | 2002080429 A | 3/2002 |
|---|---|---|
| WO | 2008032531 A1 | 3/2008 |

OTHER PUBLICATIONS

Schultz et al. J. Org. Chem. (1977), vol. 42, pp. 3459-3460.*
Ryu, Seungmin; Jackson, John A. and Thompson, Charles M. Methanolysis of Phosphoramidates with Boron Trifluoride-Methanol Complex, J. Org. Chem., 1991, vol. 56, pp. 4999-5002, 1991 American Chemical Society.
Meier, Chris cycloSal-Pronucleotides—Design of Chemical Trojan Horses Mini Reviews in Medicinal Chemistry, 2002, vol. 2, No. 3, pp. 219-234 2002 Bentham Science Publishers, Ltd.
Hall, Richard C. and Inch, Thomas D. 1979 'Asymmetric Tetracoordinate Pentacovalent Organophosphorus Compounds: Their Resolution and Determination of Enantiomeric Purity', Phosphorus, Sulfur, and Silicon and the Related Elements, 7:2, vol. 7, pp. 171-184 URL: http://dx.doi.org/10.1080/03086647908077464.
Wu, Feiyue; Li, Wen-Shan; Chen-Goodspeed, Misty; Sogorb, Miguel A.; Raushel, Frank M. Rationally Engineered Mutants of Phosphotriesterase for Preparative Scale Isolation of Chiral Organophosphates J. Am. Chem. Soc. 2000, vol. 122, No. 41, pp. 10206-10207.
Meier, Chris cycloSal Phosphates as Chemical Trojan Horses for Intracellular Nucleotide and Glycosylmonophosphate Delivery—Chemistry Meets Biology Eur. J. Org. Chem. 2006, pp. 1081-1102 2006 Wiley-VCH Verlag GmbH & Co. KGaA, Weinheim.
International Preliminary Report on Patentability Dated Oct. 5, 2010.

\* cited by examiner

*Primary Examiner* — Patrick Lewis
(74) *Attorney, Agent, or Firm* — Patent Central LLC; Stephen A. Pendorf

(57) ABSTRACT

The present invention relates to a method for stereoselective synthesis of phosphorus compounds, whereby in the first reaction step a chiral auxiliary on the phosphorus atom of phosphoryl chloride, thiophosphoryl chloride or phosphorus trichloride is covalently bonded, the product from the first reaction step is reacted in the following step with an alcohol, thiol, or amine as the nucleophile in the presence of a base, and in the last step the chiral auxiliary is displaced from the product of the following step by a nucleophile.

18 Claims, No Drawings

METHOD FOR THE STEREOSELECTIVE SYNTHESIS OF PHOSPHORUS COMPOUNDS

The invention relates to a method for stereoselective synthesis of phosphorus compounds, in particular phosphate triesters.

Chiral phosphorus compounds are of great importance in catalysis as ligands, for example, in plant protection and in medicine. CycloSaligenyl nucleoside monophosphates (cycloSal NMPs), for example, form a group of nucleotide prodrugs which can be used for combating viral diseases (AIDS, herpes, Epstein-Barr virus, hepatitis, varicella zoster virus) (C. Meier; MiniRev. Med. Chem. 2002, 2, 219-234). However, with the synthesis strategies known so far in the state of the art, all cycloSal NMPs are obtained as diastereomer mixtures (C. Meier; Eur. J. Drg. Chem., 2006, 1081-1102). Only in very few cases is it possible to separate them into pure stereoisomers. It has been demonstrated in these cases that the isolated diastereomers sometimes exhibit great differences in properties with respect to antiviral activity, hydrolysis stability and toxicity (C. Meier, M. Lorey, E. De Clercq, J. Balzarini; J. Med. Chem., 1998, 41, 1417-1427).

Approval of a diastereomer mixture as a pharmaceutical active ingredient is much more complex and cost-intensive in comparison with approval of a stereoisomer-pure compound due to the substantial expansion in the physiological tests to be performed (adsorption, distribution, metabolism and excretion of each individual stereoisomer and the isomer mixtures). In recent years, this has led to an increase in approval of stereoisomer-pure active ingredients in comparison with stereoisomer mixtures.

Basically three strategies are known in the state of the art for synthesis of chiral phosphorus compounds:
1. Asymmetrical synthesis
2. Separation of stereoisomers
3. Enzymatic transformation In asymmetrical synthesis, the most common route leads to synthesis of isomer-pure P(III) and P(IV) compounds by way of introduction of a bidental chiral auxiliary, which is displaced from the phosphorus atom step by step by the desired substituents (see C. R. Hall, T. D. Inc; Phosphorus, Sulfur & Related Elements, 1979, 7, 171-84). Commercially available or readily accessible amino alcohols and sugar derivatives are used as the leading structure for these chiral auxiliaries. For example, L-ephedrine is often used as such a chiral auxiliary. However, dispensing of L-ephedrine in Germany is subject to the [German] Precursors Control Act, so its use is usually limited to academic studies because of the increased bureaucratic complexity. In addition, the P—O bond break constitutes a severe restriction, so that only asymmetrical synthesis of diastereomer-pure thioates is possible today. However, this synthesis strategy fails with stereoisomer-pure phosphate triesters.

In stereoisomer separation, derivatives of the naturally occurring amino acid L-proline and its antipode D-proline are often used for synthesis of separable diastereomer mixtures (S. Ryu, J. A. Jackson, C. M. Thompson; J. Org. Chem. 1991, 56, 4999-5002). In general, reactive phosphorus compounds are reacted with these proline derivatives to form a phosphoric acid amidate, which can be separated into its diastereomers by crystallization or chromatographic separation. The disadvantage of this strategy is, on the one hand, the atom economic inefficiency (max. 50% yield, one diastereomer must always be discarded), while on the other hand, only structurally simple phosphate triesters can be synthesized. It is for instance impossible to use acid-labile substituents.

The use of enzymes for kinetic racemate cleavage of chiral phosphoric acid analogs is a relatively recent field of research, so that very few approaches have been published so far (see, for example, F. Wu, W.-S. Li, M. Chen-Goodspeed, M. A. Sogorb, F. M. Raushel; J. Am. Chem. Soc. 2000, 122, 10206-07). Here again, there is a disadvantage in the inefficient atom economy because the unwanted isomer constitutes half of the reaction mixture and then must be separated from the desired isomer by corresponding enzymes. Furthermore the enzymes must be optimized for the respective molecule by mutation.

There is thus a high demand for an improved method for synthesis of isomer-pure chiral phosphorus compounds, for example, chiral organophosphorus compounds, such as phosphate triesters. The object of the present invention is thus to provide such a method which will not have the disadvantages of the state of the art and in particular will be more efficient in terms of atom economy than the methods known in the past.

According to the invention, this object is achieved by the method having the features of claim 1.

The invention provides a method for stereoselective synthesis of phosphorus compounds of formulas I through V:

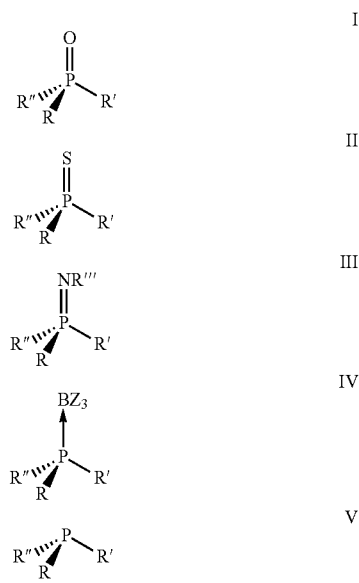

wherein
R, R' and R" are different and denote H, OH, SH, $NH_2$, alkyl, aryl, alcoholate, phenolate, thiolate, thiophenolate, primary amine, secondary amine or halide, or the residues R and R" together form a substituted or unsubstituted aliphatic or aromatic, homocyclic or heterocyclic ring system,
R''' denotes H, OH, $NH_2$, alkyl, aryl or alcoholate, and
Z denotes H, alkyl or aryl,
characterized in that
a) in the first reaction step, a chiral auxiliary of formula (VI)

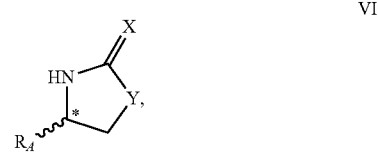

wherein

X denotes NH, NCN, O or S,

Y denotes NH, N(R$^1$), O or S, where R$^1$ is H, alkyl or aryl,

R$_A$ denotes alkyl or aryl, and

* stands for R— or S— configuration, is covalently bonded to the phosphorus atom of phosphoryl chloride, thiophosphoryl chloride or phosphorus trichloride, b) in the following step, an alcohol, thiol or amine is reacted as a nucleophile (Nu1) with the product of the first reaction step in the presence of a base, and c) in the last step, the chiral auxiliary (VI) is displaced by a nucleophile (Nu2).

The terms used here are used with their conventional technical meanings unless explicitly stated otherwise or unless something different is clearly apparent from the context.

The terms "stereoselective" or "stereospecific" in conjunction with the inventive method, for example, mean that in synthesis of a compound which occurs in various stereoisomeric forms, a stereoisomer is preferred and is thus formed in excess. A "stereoselective" or "stereospecific" reaction is specified when the reaction leads to a percentage stereomeric excess of >0%. A pure stereoisomer is spoken of here when the percentage stereoisomeric excess is >95%.

A "stereoisomer" ("stereomer") is understood to be a compound which has the same constitution, i.e., the same molecular formula and linkage of the atoms (structure) but has a different configuration or conformation, i.e., a different spatial arrangement of atoms in comparison with another compound. In the case of configurational isomers, conversion of the isomers to the respective other isomer is possible only by breaking and rejoining covalent bonds; in the case of conformational isomers (conformers), one isomer may be converted to the other by free rotation about single bonds. For characterization of the configuration of stereoisomers and/or atoms within stereoisomers, the R—S nomenclature according to the Cahn-Ingold-Prelog system is generally used. The letters "R" (from the Latin "rectus") and "S" (from the Latin "sinister") characterize the respective isomers. An index may be attached, depending on whether the term refers to a carbon or phosphorus atom, for example. "R$_C$" thus denotes the R configuration on the carbon atom, while "S$_P$" denotes the S configuration on the P atom.

"Enantiomers" are understood to be stereoisomers, which relate to one another like an image and its mirror image and do not have any plain of symmetry within the molecule. This applies to corresponding conformational and configurational isomers (conformational and configurational enantiomers). Configurational enantiomers differ in all stereocenters and are always chiral. In the present patent application, the term "enantiomer" is used as synonymous with configurational enantiomers, unless otherwise stated explicitly or unless otherwise apparent from the context for those skilled in the art.

"Diastereomers" (diastereoisomers) are stereoisomers, which are not enantiomers. Diastereomers do not behave like image and mirror image and may be either chiral or achiral. In the case of diastereomers, conformational and configurational diastereomers can be differentiated. Configurational diastereomers having several stereocenters differ from one another in at least one stereocenter but not all stereocenters. In the present patent application, the term "diastereomer" is used as synonymous with configurational diastereomer, unless otherwise indicated explicitly or unless some other meaning is apparent from the context for those skilled in the art.

"Stereocenter" refers to atoms having different substituents. Carbon, nitrogen and phosphorus, for example, may form stereocenters. In the case of carbon, for example, we speak of a stereocenter when the carbon atom has four different substituents. In the case of phosphorus, for example, there may also be a stereocenter when the phosphorus atom has three different substituents and one nonbonding electron pair. Stereocenters are often indicated with "*".

The term "chiral" here refers to molecules which are not identical to their mirror image, i.e., they cannot be made to coincide. Chiral molecules often but not necessarily have at least one stereocenter.

The term "racemate" here is understood to refer to a mixture of equal proportions of stereomers, i.e., in enantiomers or diastereomers.

The term "stereomeric excess" is understood to refer to the quantity or mass ratio of a stereomer to the corresponding other stereoisomer in a mixture of two stereomers, e.g., as the result of a stereoselective reaction. The percentage "stereomeric excess" s.e. describes the percentage product ratio of stereoisomers A and B according to the equation $$s.e. = \frac{|m(A) - m(B)|}{m(A) + m(B)} \cdot 100,$$

where m(A) is the mass of stereoisomer A, and m(B) is the mass of stereoisomer B.

If A and B are diastereomers, this is spoken of as a "diastereomeric excess" d.e., which indicates the product ratio of diastereomers A and B in a diastereoselective reaction. If A and B are enantiomers, this is spoken of as an "enantiomeric excess" e.e., which indicates the product ratio of enantiomers A and B in an enantioselective reaction. For example, a diastereomeric excess d.e. of 80% means that the mixture consists of 90% of one diastereomer and 10% of the other diastereomer. The 80% thus indicates only the excessive amount of the one diastereomer. Racemates thus have a stereomeric excess of 0%, so that there is a stereomeric excess of 100% when there is only one single stereoisomer The term "auxiliary" here is understood to refer to a group or compound covalently bonded to a molecule, allowing or facilitating a certain reaction or influencing its stereochemical course. The auxiliary may be split off again in another step after a successful reaction. A "chiral auxiliary" is understood to be a compound or group that is chiral and functions as an auxiliary. With the help of a chiral auxiliary, the course of a reaction, which is optionally nonstereoselective, is controlled so that a stereoisomer is nevertheless preferably obtained after splitting off the auxiliary.

The term "atom economy" or "atom efficiency" is understood to refer to the percentage amount of atoms converted from the starting materials to the products in a chemical reaction.

The term "nucleophile" is familiar to those skilled in the art and has the meaning customarily known to those skilled in the art here. A nucleophile is understood in particular to be a molecule which has a negatively polarized region, a negatively polarized functional group or a free electron pair, usually in a high-energy orbital. The term also includes molecules that are nucleophilic, i.e., have a relatively greater number of electrons in relation to a reactant in question and/or in relation to a region of the reactant. The reactant is also referred to as electrophilic because it receives electrons from the nucleophile. Nucleophiles may form covalent bonds by supplying electrons to a reactant. The electrons needed for the bond usually originate only from the nucleophile. Nucleophiles may be negatively charged (anions). Examples of typical nucleophilic reagents include carbanions, anions, Lewis bases, aromatics, alcohols, amines, and compounds with olefinic double bonds. The strength of the nucleophilicity depends on the reactant, the basicity, the solvent and steric factors. Those skilled in the art are aware of factors which influence the nucleophilicity of a compound and can therefore easily determine its nucleophilic properties. The nucleophilicity of a molecule is advantageously based on the strongest nucleophilic atom and/or the strongest nucleophilic functional group. However, it may equally be based on a selected atom or a selected group, which should enter into a certain reaction with a compound.

A "nucleoside" is understood here to refer to organic molecules consisting of a sugar residue and an organic base, e.g., a heterocyclic organic base, in particular a nitrogen-containing heterocyclic organic base. The sugar residue is usually a pentose, e.g., deoxyribose or ribose, but may also be some other sugar. A "nucleobase" is understood to refer to organic bases that occur in RNA or DNA. Nucleobases are often purines (R) and pyrimidines (Y). Examples of purines include guanine (G) and adenine (A); examples of pyrimidines include cytosine (C), thymine (T) and uracil (U). Phosphorylated nucleosides, for example, nucleoside monophosphate (NMP), nucleoside diphosphate (NDP) and nucleoside triphosphate (NTP), are also referred to as nucleotides. The phosphate, diphosphate (pyrophosphate) and/or triphosphate group is usually linked to the 5'-C atom of the sugar component of the nucleoside but may also be linked to the 3'-C atom, for example.

A "nucleoside analog" is understood here to be a compound which does not occur naturally in the human body, but is so similar structurally to a nucleoside that occurs naturally in the human body that it is processed by the cells and/or viral enzymes essentially according to the natural nucleoside; for example, it is phosphorylated and incorporated into an RNA or DNA strand. A nucleoside analog may itself be a nucleoside. However, it may also be another compound having the above properties, for example, a compound of a heterocyclic base and a residue that is not a sugar. Examples of nucleoside analogs include, e.g., AZT (3'-azido-2',3'-dideoxythimidine, azidothymidine), 2',3'-dideoxyinosine (didanosine), 2',3'-dideoxycytidine (zalcitabine) and 2-amino-9-((2-hydroxyethoxy)methyl)-1H-purin-6(9H)-one (acyclovir). Nucleoside phosphonates may also be nucleoside analogs.

The term "alkyl" refers to saturated aliphatic groups, including linear alkyl groups (e.g., methyl, ethyl, propyl, butyl, pentyl, hexyl, heptyl and octyl), branched alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl-substituted cycloalkyl groups and cycloalkyl-substituted alkyl groups. "Alkyl" also includes alkyl groups having oxygen, nitrogen, sulfur or phosphorus atoms, which replace one or more carbon atoms of the hydrocarbon structure. The term "alkyl" also includes both unsubstituted alkyls and substituted alkyls, where the latter refers to alkyl residues having substituents, which replace one hydrogen atom on one or more carbons of the hydrocarbon structure. Such substituents may include, for example: alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfate, alkylsulfinyl, sulfonato, sulfamoyl, sulfonamido, nitro, trifluoromethyl, cyano, azido, heterocyclyl, alkylaryl or an aromatic or heteroaromatic residue. Cycloalkyls may also be substituted, e.g., with the substituents listed above. An "alkylaryl" or an "aralkyl" residue is an alkyl substituted with an aryl (e.g., phenylmethyl (benzyl)). "Alkyl" also includes the side chains of natural and unnatural amino acids.

"Aryl" is understood to refer to groups having an aromaticity, including 5- and 6-membered aromatic single-ring groups, which may contain zero to four heteroatoms as well as multicyclic systems with at least one aromatic ring. Examples of aryl groups include benzene, phenyl, pyrrole, furan, thiophene, thiazole, isothiazole, imidazole, triazole, tetrazole, pyrazole, oxazole, isoxazole, pyridine, pyrazine, pyridazine and pyrimidine and the like. In addition, the term "aryl" includes multicyclic aryl groups, e.g., tricyclic and bicyclic groups, e.g., naphthalene, benzoxazole, benzodioxazole, benzothiazole, benzimidazole, benzothiophene, methylenedioxyphenyl, quinoline, isoquinoline, napthyridine, indole, benzofuran, purine, benzofuran, deazapurine or indolizine. "Aryl" is also understood to include aryl groups having heteroatoms in the ring structure ("heteroaryls"). The aromatic ring may be substituted in one or more ring positions. Aryl groups may also be fused or bridged with alicyclic or heterocyclic rings which are not aromatic, thus forming a multicyclic system (e.g., tetraline, methylenedioxyphenyl).

"Alcoholate" is understood to refer to alcohol residues R—O—. "Alcohols" are compounds according to the formula R—OH, where R may be any organic residue, i.e., a residue formed by an organic compound, optionally with other hydroxyl groups, for example, an alkyl or aryl residue. "Phenolate" is understood to be an aromatic hydroxyl compound whose OH group(s) sit(s) on the aromatic ring, e.g., $C_6H_5$—O. "Thiolates" are compounds of the formula R—S—, where R may be any organic residue, for example, an alkyl or aryl residue. Thiolates correspond to alcoholates, where the oxygen of the hydroxyl group is replaced by sulfur. "Thiophenolates" are phenolates according to the above definition with the provision that the oxygen of at least one hydroxyl group is replaced by sulfur. "Thiols" are compounds of the formula R—SH, optionally with other SH groups, where R may be any organic residue, for example, an alkyl or aryl residue.

"Amines" are derivatives of ammonia ($NH_3$), where one or more of the hydrogen atoms of ammonia have been replaced by organic residues, e.g., alkyl or aryl residues. "Primary amines" are amines in which only one of the hydrogen atoms has been replaced by an organic residue, e.g., an alkyl or aryl residue. "Secondary amines" are amines in which two of the hydrogen atoms are replaced by an organic residue, e.g., an alkyl or aryl residue.

A "halide" is understood to refer to halogen residues, e.g., F—, Cl—, Br—, I— and At—.

The term "base" is also familiar to those skilled in the art and comprises compounds or substances which have a free electron pair with which it can form a covalent bond to an atom, molecule or ion (electron pair acceptor, Lewis base). This term also includes a molecule or ion having a free electron pair with which it can attract and hold protons (proton acceptor, Brönsted base). This term also includes substances which lead to the formation of the anion that is characteristic of the respective solvent in an aqueous solution, for example, the hydroxide ion, and form the solvent, e.g., water, in reaction with the corresponding acid by neutralization (Arrhenius base).

The inventive method for stereoselective synthesis of phosphorus compounds, in particular organophosphorus compounds such as phosphorus triesters, is based on the use of a chiral auxiliary according to the following formula VI:

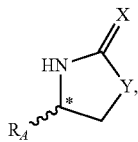
VI wherein
X denotes NH, NCN, O or S,
Y denotes NH, N(R¹), O or S, wherein R¹ denotes H, alkyl or aryl,
$R_A$ denotes alkyl or aryl and
*stands for R— or S— configuration.

The chiral auxiliary according to formula VI, which may be present in the $R_C$ or $S_C$ configuration, leads to a high induction on the phosphorus atom and may be substituted under mild reaction conditions.

"Induction" here refers to the so-called inductive effect (I effect) with which those skilled in the art are familiar and which refers to a charge-altering "electron-attracting" or "electron-displacing" effect of a functional group or an atom. The inductive effect is based on differences in electronegativity between atoms or functional groups of a molecule, which leads to polarization of atom bonds.

One example of an auxiliary that falls under the above formula VI is $S_C$-4-isopropyl-2-mercapto-2-thiazoline 1:

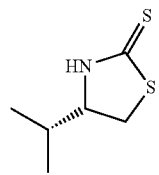
1

Other derivatives of compound VI can be synthesized easily by those skilled in the art and may optionally also be selected or implemented in a targeted manner for the desired intended purpose. The reaction conditions under which the chiral auxiliary VI is reacted with phosphoryl chloride or thiophosphoryl chloride 2 to form the corresponding reaction product 10, which is also referred to below as an active ester, may optionally be optimized easily by those skilled in the art with respect to the solvent, the base used, the reaction temperature and reaction time, without requiring more than mere routine experiments to do so.

In the following step, any alcohols, thiols or amines may be used as the nucleophile (Nu1), so that the corresponding esters 11, thioesters 12, amidates and/or diamidates 13 are formed, as shown in the following, for example:

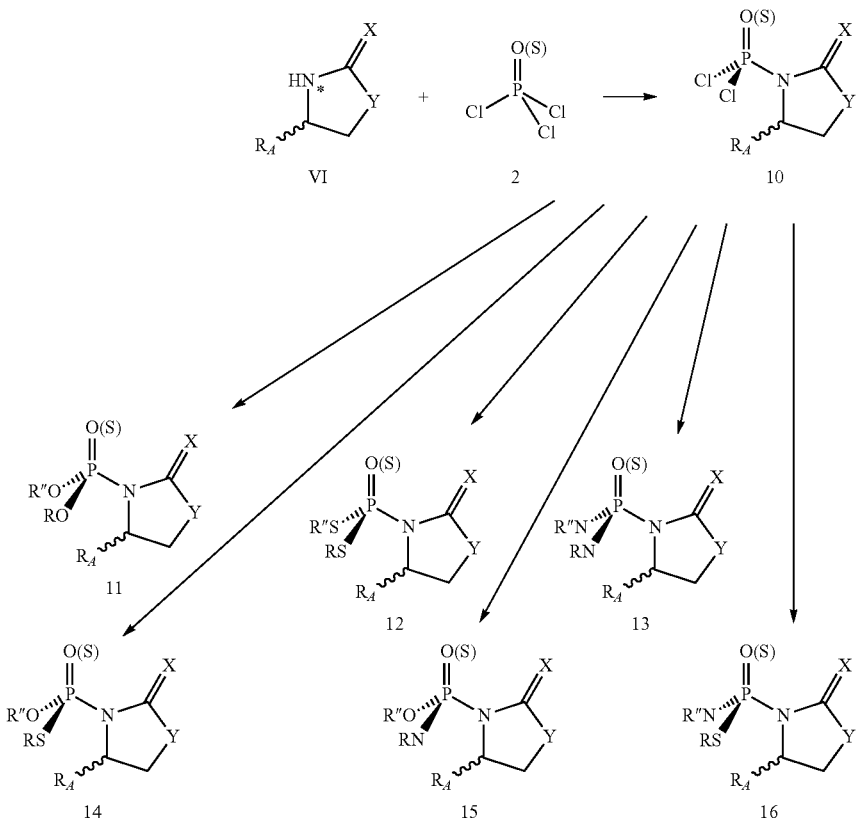

In addition, the mixed compounds 14-16 can also be synthesized. In this reaction, it is important that a base is also present in addition to the nucleophile (Nu1). Depending on the alcohol, thiol and/or amine, the yield of the reaction can be influenced by the differing strengths of the base used. In the reactions represented above, it is important on the whole that induction is also observed in these reactions due to the chiral auxiliary VI, which is covalently bonded to the phosphorus atom, so that compounds 11-16 are all chiral with respect to the stereochemistry on the P atom. However, achiral phosphate derivatives may of course also be synthesized by this method. A nucleophile (Nu1), which is especially preferred in the following step, is salicyl alcohol (2-hydroxybenzyl alcohol).

In the last step, the five-membered ring heterocycles used as the chiral auxiliaries VI are displaced by a nucleophile (Nu2). There is an inversion of the configuration on the phosphorus atom, so that chiral phosphates are formed on the whole if the product of the active ester and the nucleophile (Nu2) used in the following step is also chiral. The reaction conditions are to be adapted to the auxiliaries used, but that is readily possible for those skilled in the art on the basis of their technical expertise, optionally by performing routine experiments. The properties of the departing groups can be modified in a targeted manner by an additional metal salt activation. For example, the use of mercury salts with auxiliaries containing sulfur can be mentioned here. Copper salts are suitable for oxygen-containing auxiliaries.

Consequently, chiral phosphoric acid derivatives can be formed by stepwise replacement of the chlorine atoms bound to the phosphorus atom at the beginning of the reaction. If one starts with the corresponding thiophosphoryl chloride at the beginning, a plurality of chiral thiophosphoric acid compounds can thus be synthesized.

With the help of the inventive method, compounds I-V can be synthesized:

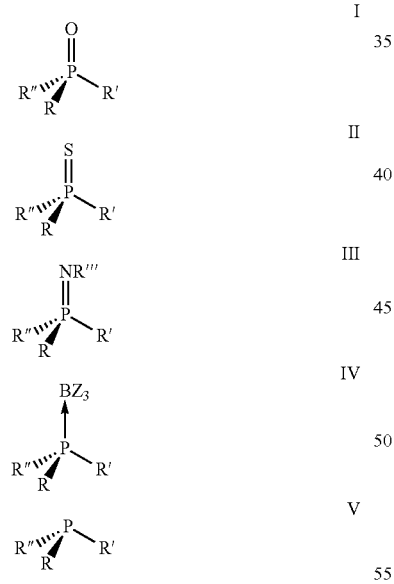

where the residues R, R' and R" also are or may contain different isotopes of an element, for example.

A number of target compounds which can be synthesized by the novel method (Nucl=nucleoside) are shown below as examples. These include, for example, compounds that are of great interest for use as pharmaceuticals (e.g., 18 or 19). This pertains to the field of nucleotide prodrugs just as well as the field of antisense oligonucleotides. Furthermore, this method may also be used for synthesis of chiral phosphorus (III) compounds. Such chiral compounds are of enormous interest as ligands in metal-catalyzed reactions.

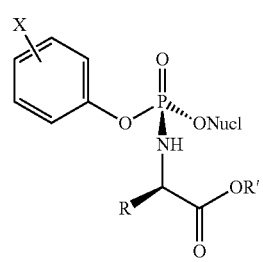

X = electron acceptor
R = alkyl; R' = alkyl, aryl

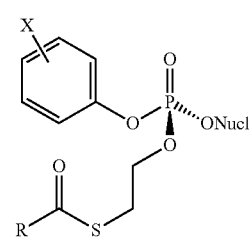

X = electron acceptor
R = alkyl; R' = alkyl, aryl

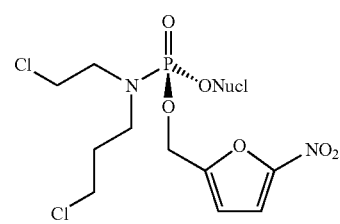

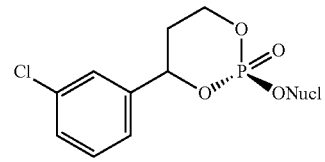

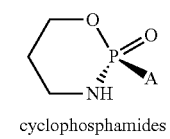

cyclophosphamides

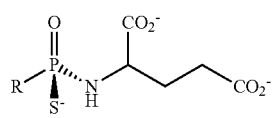

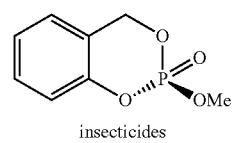

insecticides

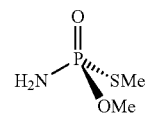

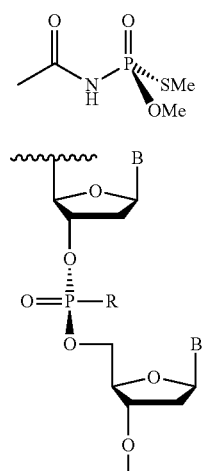

R = SH, alkyl
B = base
antisense

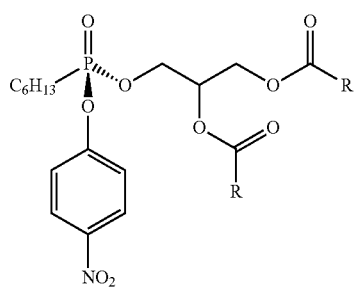

transition
state
analogs

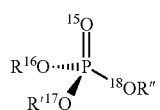

R ≠ R' ≠ R" = H, alkyl, aryl

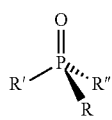

R ≠ R' ≠ R" = H, alkyl, aryl
cyclic, acyclic
P-chiral ligands

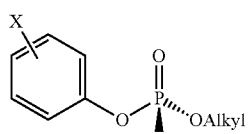

lipase inhibitor
R = alkyl, aryl, glycerol
residues

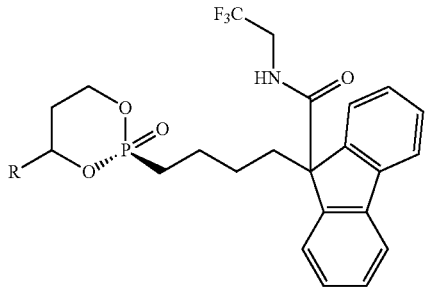

MTP = microsomal
triglyceride transfer
proteine

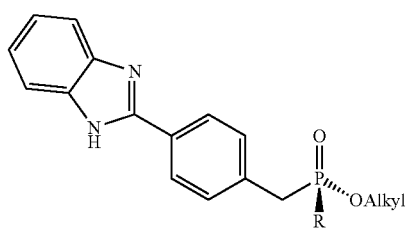

coronary
vasodilator
R = NR'R"

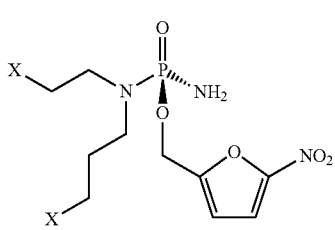

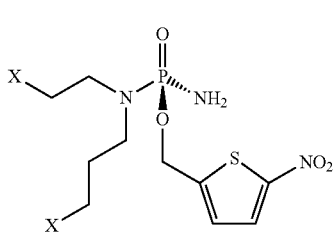

X = H, alkyl, aryl, halide

The following chiral, nonracemic phosphorus compounds, for example, can be synthesized by the inventive method:
1. Derivatives of phosphoric acid (esters, amidates)
2. Derivatives of phosphonic acid (esters, amidates)
3. Derivatives of phosphinic acid (esters, amidates)
4. Derivatives of thiophosphoric acid (esters, amidates)
5. Derivatives of thiophosphonic acid (esters, amidates)
6. Derivatives of thiophosphinic acid (esters, amidates)
7. Phosphazanes
8. Phosphazenes
9. Halophosphoric acids (esters, amidates)
10. Dihalophosphoric acid (esters, amidates)
11. Phosphoryl halides (esters, amidates)
12. Halothiophosphoric acids (esters, amidates)
13. Dihalothiophosphoric acid (esters, amidates)
14. Thiophosphoryl halides
15. Phosphites, phosphines, phosphorus amidites
16. Borano derivatives 17. Pepsin and penicillopepsin inhibitors, peptide analogs
18. Aminophosphonates, aminophosphinates, lipase inhibitors, peptide mimetics, antagonists of carboxylic acid derivatives
19. Cyclophosphamides, P-chiral phosphine ligands The starting materials required to perform these reactions are usually easily and favorably accessible. In addition, it should also be possible to perform the reactions on a large scale.

In a preferred embodiment, a stereoisomer formed in excess in the following step b) in the inventive method should first be purified and used in this purified form in the last step c). In this way, the unwanted reaction of the nucleophile (Nu2) with the stereoisomer which is present in a less than stoichiometric amount can be largely avoided and the atom economy of the reaction can be further improved.

The nucleophile (Nu2) used in step c) may be, for example, a nucleophile, which is selected from the group consisting of nucleoside, nucleoside monophosphate, nucleoside diphosphate, nucleoside triphosphate, nucleoside analog, nucleoside monophosphate analog, nucleoside diphosphate analog, nucleoside triphosphate analog, phosphate, pyrophosphate, glycosyl phosphate and α-deprotonated glycosyl or salts thereof.

In an especially preferred embodiment of the inventive method, 4-isopropyl-2-mercapto-2-thiazoline is preferably used as the chiral auxiliary (VI) and is covalently bonded to the phosphorus atom of phosphoryl chloride, forming ($S_C$)—N-dichlorophosphoryl-4-isopropyl-2-mercapto-2-thiazoline. ($S_C$)—N-Dichlorophosphoryl-4-isopropyl-2-mercapto-2-thiazoline is then reacted with salicyl alcohol in the following step b), the resulting ($R_P$,$S_C$)— and ($S_P$,$S_C$)-diastereomers are separated and the chiral auxiliary (VI) is then displaced by a nucleoside, forming cycloSaligenyl nucleoside monophosphate from the ($R_P$,$S_C$)-diastereomers.

With the inventive method, it is possible for the first time to gain synthetic access to the diastereomer-pure cycloSal NMPs. The inventive method is impressive due to the short synthesis sequence and its potential applicability for many cycloSal NMPs. The inventive method thus allows isomer-pure synthesis of cycloSal nucleotide prodrugs, which may have extremely interesting properties with regard to antiviral activity, for example, and are of great interest for pharmaceutical application.

A nucleoside used as the nucleophile (Nu2) in step c) is preferably selected from the group consisting of adenosine, guanosine, cytidine, thymidine, uridine, deoxyadenosine, deoxyguanosine, inosine, deoxycytidine, deoxyuridine, deoxythymidine, 2-thiocytidine, $N^4$-acetylcytidine, 2'-O-methylcytidine, 3-methylcytidine, 5-methylcytidine, 2-thiouridine, pseudo-uridine, dihydrouridine, 5-(carboxyhydroxymethyl)-uridine, 5-carboxymethylaminomethyluridine, 5-methylaminomethyluridine, 5-methoxycarbonylmethyluridine, 5-methoxyuridine, ribothymidine, 1-methyladenosine, 2-methyladenosine, $N^6$-methyladenosine, inosine, 1-methylinosine, guanosine, $N^2$-2,2-dimethylguanosine, $N^2$-2-methylguanosine, $7^+$-methylguanosine and 2'-O-methylguanosine.

The percentage stereomeric excess after following step b) in the inventive method is especially preferably ≧10%, preferably ≧20%, more preferably ≧30%, ≧40%, ≧50% or ≧60%, and especially preferably ≧70%, ≧75%, ≧80%, ≧85% or ≧90%.

A purification, for example, chromatographic purification, which is performed subsequently especially leads to a percentage stereomeric excess of ≧95%, preferably ≧96%, more preferably ≧97% or ≧98%, especially preferably ≧99%, ≧99.5%, ≧99.6%, ≧99.7%, ≧99.8% or ≧99.9%.

The invention is described in greater detail below on the basis of an exemplary embodiment for illustration purposes.

EXAMPLE 1

Diastereoselective Synthesis of Stereoisomer-Pure cyclosal NMPS

The stereoselective synthesis of a stereoisomer-pure cycloSal NMP (cycloSaligenyl nucleoside monophosphate) is diagramed schematically below for illustration purposes:

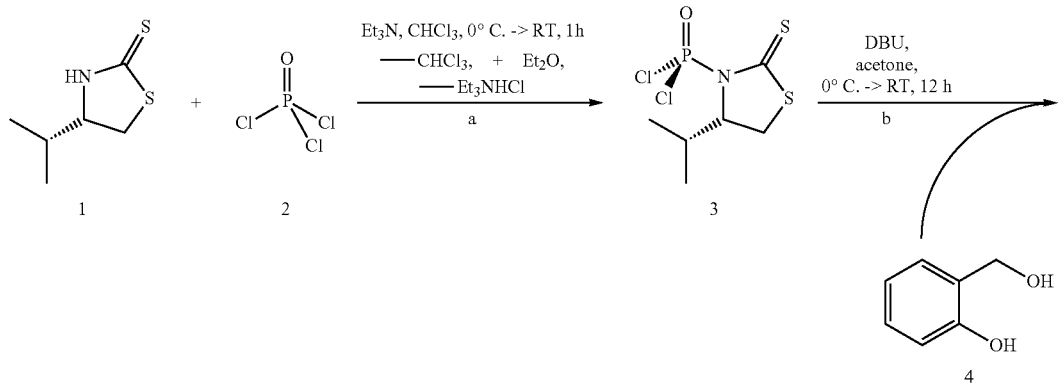

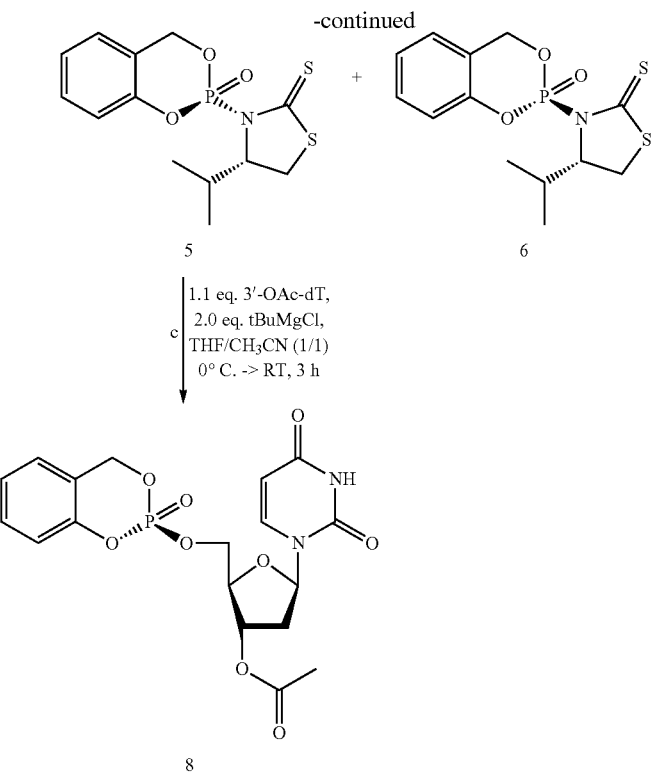

The inventive approach for diastereoselective synthesis of cycloSal NMPs is based on the use of the chiral auxiliary $S_C$-4-isopropyl-2-mercapto-2-thiazoline 1, which leads to high induction on the phosphorus atom and can be substituted under mild reaction conditions, so that isomer-pure cycloSal NMPs can be obtained in a three-step reaction sequence.

To do so, the chiral auxiliary 1 is reacted with phosphoryl chloride 2 in step a) to form $(S_C)$—N-dichlorophosphoryl-4-isopropyl-2-mercapto-2-thiazoline 3. This is done in chloroform with triethylamine as the proton scavenger at 0° C. in almost quantitative yield. Because of the high reactivity of product 3, the resulting triethylammonium hydrochloride is filtered out under inert reaction conditions, and product 3 is then reacted immediately. Product 3 was coupled to salicyl alcohol 4 in step b) in a 43% yield. The diastereomeric excess d.e. amounted to 88% and the diastereomers 5 ($R_P,S_C$) and 6 ($S_P,S_C$) were obtained as pure isomers by chromatographic purification (>95% d.e., determined by NMR integration). To do so, 3 was dissolved in acetone with 4 and mixed with a solution of 1,8-diazabicyclo[5.4.0]undec-7-ene (DBU) in acetone at 0° C. and stirred for 12 hours at room temperature. The subsequent substitution of the chiral auxiliary from active amide 5 by the nucleoside 3'-O-acetylthymidine led to diastereomer-pure $S_P$-cycloSal NMP 8 in a 48% yield. To do so, the nucleoside 3'-O-acetylthymidine was dissolved in a THF/acetonitrile mixture (1/1) and deprotonated with the base tert-butylmagnesium chloride (t-BuMgCl). The resulting suspension was added slowly to the ($R_P,S_C$) active imide 5 (dissolved in a THF/acetonitrile mixture, 1/1). After three hours, the reaction was terminated and product 8 was purified chromatographically.

The invention claimed is:

1. A method for stereoselective synthesis of phosphorus compounds of formulas I through V:

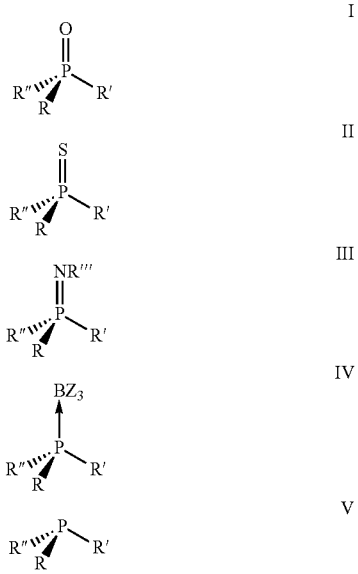

wherein
R, R' and R" are different and denote H, OH, SH, $NH_2$, alkyl, aryl, alcoholate, phenolate, thiolate, thiophenolate, primary amine, secondary amine or halide, or the residues R and R" together form a substituted or unsubstituted aliphatic or aromatic, homocyclic or heterocyclic ring system, R''' H, OH, $NH_2$, alkyl, aryl or alcoholate, and Z denotes H, alkyl or aryl,
wherein a) in the first reaction step, a chiral auxiliary of formula (VI):

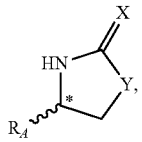

wherein
X denotes NH, NCN, O or S,
Y denotes NH, N($R^1$), O or S, wherein $R^1$ is H, alkyl or aryl,
$R_A$ denotes alkyl or aryl, and
* stands for the R or S configuration,
is covalently bonded to the phosphorus atom of phosphoryl chloride, thiophosphoryl chloride or phosphorus trichloride,
b) in the following step, an alcohol, thiol or amine as the nucleophile (Nu1) is reacted with the product of the first reaction step in the presence of a base, and
c) in the last step, the chiral auxiliary (VI) is displaced by a nucleophile (Nu2).

2. The method according to claim 1, wherein a stereoisomer formed in excess in step b) is purified and used in step c).

3. The method according to claim 1, wherein the nucleophile (Nu2) used in step c) is selected from a group consisting of nucleoside, nucleoside monophosphate, nucleoside diphosphate, nucleoside triphosphate, nucleoside analog, nucleoside monophosphate analog, nucleoside diphosphate analog, nucleoside triphosphate analog, phosphate, pyrophosphate, glycosyl phosphate and α-deprotonated glycosyl, or salts thereof.

4. The method according to claim 3, wherein 4-isopropyl-2-mercapto-2-thiazoline is used as the chiral auxiliary (VI) and is covalently bonded to the phosphorus atom of phosphoryl chloride, forming ($S_C$)-N-dichlorophosphoryl-4-isopropyl-2-mercapto-2-thiazoline, ($S_C$)-N-dichlorophosphoryl-4-isopropyl-2-mercapto-2-thiazoline is reacted with salicyl alcohol in the following step b), the resulting ($R_P,S_C$)- and ($S_P,S_C$)-diastereomers are separated and the chiral auxiliary (VI) is then displaced from the ($R_P,S_C$) diastereomer by a nucleoside, forming cycloSaligenyl nucleoside monophosphate.

5. The method according to claim 3, wherein the nucleoside is selected from the group consisting of adenosine, guanosine, cytidine, thymidine, uridine, deoxyadenosine, deoxyguanosine, inosine, deoxycytidine, deoxyuridine, deoxythymidine, 2-thiocytidine, $N^4$-acetylcytidine, 2'-O-methylcytidine, 3-methylcytidine, 5-methylcytidine, 2-thio-uridine, pseudouridine, dihydrouridine, 5-(carboxyhydroxymethyl)-uridine, 5-carboxymethylaminomethyluridine, 5-methylaminomethyluridine, 5-methoxycarbonylmethyluridine, 5-methoxyuridine, ribothymidine, 1-methyladenosine, 2-methyladenosine, $N^6$-methyladenosine, inosine, 1-methylinosine, guanosine, $N^2$-2,2-dimethylguanosine, $N^2$-2-methylguanosine, $7^+$-methylguanosine and 2'-O-methylguanosine.

6. The method according to claim 1, wherein the percentage of stereomeric excess after step b) is $\geq 10\%$.

7. The method according to claim 1, wherein the percentage of stereomeric excess after step b) is $\geq 10\%$.

8. The method according to claim 1, wherein the percentage of stereomeric excess after step b) is $\geq 20\%$.

9. The method according to claim 1, wherein the percentage of stereomeric excess after step b) is $\geq 30\%$.

10. The method according to claim 1, wherein the percentage of stereomeric excess after step b) is $\geq 40\%$.

11. The method according to claim 1, wherein the percentage of stereomeric excess after step b) is $\geq 50\%$.

12. The method according to claim 1, wherein the percentage of stereomeric excess after step b) is $\geq 60\%$.

13. The method according to claim 1, wherein the percentage of stereomeric excess after step b) is $\geq 70\%$.

14. The method according to claim 1, wherein the percentage of stereomeric excess after step b) is $\geq 75\%$.

15. The method according to claim 1, wherein the percentage of stereomeric excess after step b) is $\geq 80\%$.

16. The method according to claim 1, wherein the percentage of stereomeric excess after step b) is $\geq 85\%$.

17. The method according to claim 1, wherein the percentage of stereomeric excess after step b) is $\geq 90\%$.

18. A method for stereoselective synthesis of phosphorus compounds of formulas I through V:

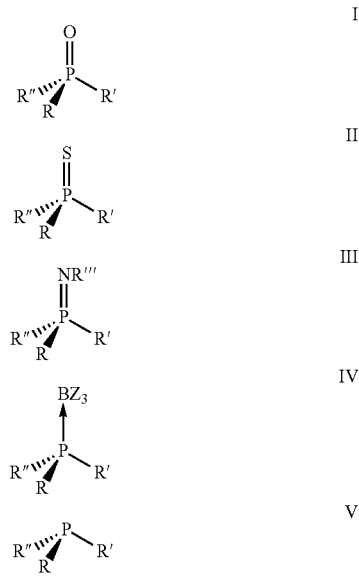

wherein
R, R' and R" are different and denote H, OH, SH, $NH_2$, alkyl, aryl, alcoholate, phenolate, thiolate, thiophenolate, primary amine, secondary amine or halide, or the residues R and R" together form a substituted or unsubstituted aliphatic or aromatic, homocyclic or heterocyclic ring system,
R'" H, OH, $NH_2$, alkyl, aryl or alcoholate, and
Z denotes H, alkyl or aryl,
wherein
a) in the first reaction step, a chiral auxiliary of formula (VI):

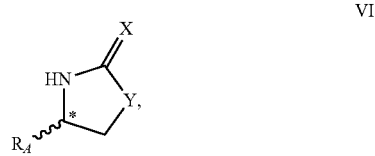

wherein
X denotes NH, NCN, O or S,
Y denotes NH, N($R^1$), O or S, wherein $R^1$ is H, alkyl or aryl,
$R_A$ denotes alkyl or aryl, and
* stands for the R or S configuration,
is covalently bonded to the phosphorus atom of phosphoryl chloride, thiophosphoryl chloride or phosphorus trichloride, b) an alcohol, thiol or amine as the nucleophile (Nu1) is reacted with the product of the first reaction step in the presence of a base, and
c) the chiral auxiliary (VI) is displaced by a nucleophile (Nu2).

* * * * *